United States Patent [19]

Haaheim

[11] Patent Number: 6,080,552
[45] Date of Patent: Jun. 27, 2000

[54] DETECTION OF ANTIBODY PRODUCTION

[76] Inventor: Lars Reinhardt Haaheim, Laboratory of Biotechnology Bergen High Technology Centre University of Bergen, N-5020 Bergen, Norway

[21] Appl. No.: 08/913,137
[22] PCT Filed: Feb. 21, 1996
[86] PCT No.: PCT/GB96/00392
  § 371 Date: Aug. 21, 1997
  § 102(e) Date: Aug. 21, 1997
[87] PCT Pub. No.: WO96/26443
  PCT Pub. Date: Aug. 29, 1996

[30] Foreign Application Priority Data

Feb. 21, 1995 [GB] United Kingdom .................. 9503406

[51] Int. Cl.$^7$ .................................................. G01N 33/53
[52] U.S. Cl. ......................... 435/7.92; 435/7.1; 435/7.2; 435/7.71; 435/7.94; 435/7.95
[58] Field of Search .................................... 435/7.1, 7.23, 435/172.2, 5, 7.2, 7.71, 7.92, 7.94, 7.95

[56] References Cited

U.S. PATENT DOCUMENTS

| | | | |
|---|---|---|---|
| 5,019,497 | 5/1991 | Olsson . | |
| 5,188,942 | 2/1993 | Reddington et al. | 435/28 |
| 5,360,719 | 11/1994 | Levine et al. | 435/29 |

FOREIGN PATENT DOCUMENTS 0 526 952 A3  2/1993  European Pat. Off. .

OTHER PUBLICATIONS

Cox et al, Vaccine, vol. 12(11), 993–999, 1994.
Atkinson et al., "Direct Measurement of Antibody Production in Cell Suspensions Using an Enzyme–Linked Immunosorbent Assay"; Journal of Immunological Methods, 76 (1985) pp. 365–373.
Hetland et al., "The Use of Flow Cytometry to Detect the Biosynthesis of Complement Components"; Journal of Immunological Methods, 140 (1991) 167–171.
Amadori et al., "Spontaneous in Vitro Production of Virus–Specific Antibody by Lymphocytes from HIV–Infected Subjects", Clinical Immunology and Immunopathology 46, 342–351 (1988).
Czerkinsky et al., The Solid Phase enzyme–Linked Immunospot Assay (ELISPOT) for Enumerating Antibody-Secreting Cells: Methodology and Applications (Cpt. 10). ELISA and Other Solid Phase Immunoassays, pp. 218–239.
Kelly et al., "The Use of the Enzyme–linked Immunosorbent Assay (ELISA) for the detection and Quantification of Specific Antibody from Cell Cultures", Immunology 1979 pp 45–52.
Greene et al., "Modification, Optimization and Simplification of the Spot ELISA Technique for the Enumeration of Cells Secreting Anti–hapten Antibodies", Journal of Immunological Methods, 129 (1990) 187–197.
Ruedl et al., "A Novel and Sensitive Method for the Detection of Secreted Cell Products Using Time–resolved Fluorescene", Journal of Immunological Methods 168 (1994) pp 61–67.
Quiding et al., Intestinal Immune Reponses in Humans, The American Society for Clinical Investigation, Inc. vol. 88, Jul. 1991 pp 143–148.
Kehrl et al., "Identification, Purification, and Characterization of Antigen–Activated and Antigen–Specific Human B Lymphocytes", Journal of Experimental Medicine, vol. 157, May 1983, pp 1693–1697.

*Primary Examiner*—Paula K. Hutzell
*Assistant Examiner*—Lin Sun-Hoffman
*Attorney, Agent, or Firm*—Pennie & Edmonds LLP

[57] ABSTRACT

The present invention provides a method of detecting active antibody production in a blood sample by contacting, in the presence and absence of protein synthesis inhibitor, aliquots of the sample with a solid phase under conditions which permit antibody production and secretion by the lymphocytes; detecting in solution, binding of antibody to the antigen(s) on the solid phase; and comparing the antibody binding in the presence or absence of protein synthesis inhibitor, whereby to obtain a determination of the amount of active antibody secretion in response to the antigen(s); and kits for performing the method. The method may also be modified to allow detection of non-specific infection indicators.

22 Claims, No Drawings

DETECTION OF ANTIBODY PRODUCTION

TECHNICAL FIELD

The present invention relates to the detection of antibody production, and in particular to the detection of active antibody synthesis in blood samples in response to infection or vaccination etc., by means of a modified enzyme-linked immunosorbent assay (ELISA).

BACKGROUND ART

ELISA has long been used to detect and measure antibody (or antigen). Most commonly, ELISA is used as a serological assay, but it is also used to study the immunochemical properties of antigens or antibodies, and has frequently found application in, for example, the evaluation and characterisation of immune responses, to investigate antibody production by cell cultures, in hybridoma technology etc.

Due to its sensitivity, simplicity and ease and speed of operation, the technique has been widely adopted as a diagnostic tool and is now routinely used in clinical laboratories to detect antibodies in serum or plasma to infectious agents, following infection or vaccination. Thus for example, many tests for HIV infection depend upon detecting antibodies to the virus in the serum or plasma of patients using a conventional ELISA assay.

However, since such a simple serological ELISA test simply measures the presence of the target antibody in the sample, it cannot distinguish between on-going antibody synthesis in response to the antigen, and antibodies already present from past infection, or by passive transfer etc. Whilst in some cases, it may suffice simply to obtain information concerning the presence of antibody, it is in other cases desirable to be able to determine whether or not the detected target antibodies are acutely synthesised by the lymphocytes at the time of testing, for example during a vaccination course, or in the diagnosis of infection in infants, to distinguish from passively transferred maternal antibodies. This cannot be achieved in a classical ELISA method.

Other methods have therefore been developed, which enable on-going antibody synthesis to be detected. Particular mention may be made in this regard of the enzyme-linked immunospot (ELISPOT) assay (also known as spot ELISA or ELISA-plaque assay), as reviewed for example by Czerkinsky et al. in ELISA and other Solid Phase Immunoassays, Ed. D. M. Kenneny and S. J. Challacombe, 1988, Chapter 10, 217–239. This technique, based on the ELISA method, enables the enumeration of lymphocytes secreting antibody against one or more target antigens. Basically, the ELISPOT is a variant of the ELISA method, whereby antibody secreting cells (ASC) may be revealed by culturing lymphocytes in specially modified ELISA wells coated with the target antigen, and by replacing the standard ELISA reagents with enzyme-substrate complexes that yield a coloured precipitate (spots), adjacent to the secreting cell. Spots can then be counted to give a measure of the number of antibody-producing cells. Protein synthesis inhibitors may be included in the culture medium, to confirm that the spots detected are due to de novo antibody synthesis, during the in vitro incubation period.

Whilst the ELISPOT technique has proved very useful in studying the dynamics of humoral immune responses, and has been used to detect spontaneous ASC that appear transiently in the peripheral circulation of immunised subjects, certain features of the method place constraints on its use in a clinical diagnostic setting. Firstly, since for each sample individual spots need to be counted which can be time consuming and laborious, the method is not particularly suited to the analysis of large numbers of samples, such as occurs in a clinical diagnostic laboratory. Secondly, only the number of cells secreting antibody in each sample is enumerated and generally speaking, this requires reasonably large sample volumes, eg. several mls. ELISPOT plates are also expensive and the assay is not readily amenable to automation.

It will be seen therefore, that despite advances in antibody detection techniques, there remains a need for an assay which is simple, quick and cost effective to perform, which reliably enables precise quantification of spontaneously secreted antibody, which is able to distinguish de novo antibody synthesis, and particularly, which may be performed on blood samples for diagnostic purposes. The present invention addresses this need.

SUMMARY OF THE INVENTION

In one aspect, the present invention therefore provides a method of detecting active antibody production in response to a target antigen in a blood sample, said method comprising:

contacting, in the presence and absence of protein synthesis inhibitor, aliquots of said sample, or optionally, of lymphocytes directly isolated from said sample, with a solid phase under conditions which permit antibody production and secretion by the lymphocytes;

detecting in solution, binding of antibody to said antigen (s) on the solid phase; and comparing said antibody binding in the presence or absence of protein synthesis inhibitor, whereby to obtain a determination of the amount of active antibody secretion in response to said antigen(s).

As used herein, "active antibody production" refers to spontaneously secreted antibodies produced by lymphocytes in the sample which are actively producing antibodies during the course of the assay as a consequence of an active ongoing immune response. In all cases the antibodies are directed to antigens which are presented in vivo and not in vitro either before or during the assay method of the invention.

As used herein the phrase "active antibody secretion in response to said antigen" is intended to mean that the actively secreted antibodies bind to the antigen used in the assay, although the antigen used may not have been the immunogen stimulating the immune response in the first place. Thus, whilst both the antigen used in the assay and the immunogen which has stimulated or is stimulating the production of antibodies in vivo would bind to the antibodies to be detected by virtue of identical or very similar epitopes, in other respects the antigen and immunogen may not be identical. Thus, whilst the antigen used in the method of the invention may be material containing all or some parts of the relevant immunogen, e.g. derived from infected individuals, or purified parts from the same or similar material, the antigen may similarly be prepared synthetically, e.g. by chemical synthesis or recombinant expression, with added or deleted portions over the native antigen. Thus fusion proteins, or molecules expressing only the appropriate epitope(s) may be used.

Generally speaking, the method of the invention involves incubating lymphocytes from the blood sample in contact with an appropriate solid surface to immobilize antibodies to be detected under conditions which permit antibody production and secretion by the lymphocytes, and then removing the cells, and detecting the binding of antibody to the antigen on the solid phase. By comparing the level of antibody binding detected, in the presence or absence of a protein synthesis inhibitor, de novo antibody synthesis may be distinguished and quantified.

Surprisingly, the method of the invention permits the use of small blood sample volumes (eg. μl volumes, less than 1 ml), directly to detect spontaneous antibody production by unstimulated lymphocytes, without a prior step of pre-culturing the lymphocytes prior to incubation with the solid phase. In other words, the lymphocytes from the sample are used directly in the assay method of the invention without any prior treatment or stimulation, e.g. in vitro stimulation by antigen. The antibodies secreted by the lymphocytes at the time of sampling may thus be detected. In this way, even using such small sample volumes, spontaneous ongoing antibody synthesis in response to the test antigen may advantageously be distinguished from bystander activation of lymphocytes. Also the lymphocytes are assayed in a situation where they spontaneously secrete antibodies, without stimulating the cells to reveal any memory. This is in contrast to other published methods which take advantage of in vitro antigenic stimulation to increase the sensitivity of the test. The present invention on the other hand takes advantage of spontaneous antibody secretion to permit the detection of antibodies in blood indicative of an ongoing infection by the test antigen; plasma lymphocytes will secrete antibody against the test antigen in the first few weeks following infection, or vaccination etc. Detection of such antibodies by the method of the present invention enables infection to be diagnosed or determined, or the antibody response to vaccination to be monitored etc. This is particularly useful in infants and neonates, where it is important to distinguish newly synthesised antibody from passively transferred maternal antibodies. The same blood sample may be analyzed for antibodies against several distinct infectious agents either in separate assays or in the same assay using multiple relevant antigens. Thus allowing for use of relevant contacting antigens consistent with the clinical syndrome with which the patient presents. In diagnosing infections, it is also important to be able to distinguish ongoing antibody synthesis from antibodies already existing from an earlier infection. Recalling immunological memory by antigenic stimulation in vitro is not consistent with an assay aimed at identifying an ongoing acute infection, and hence prior methods based on antigenic stimulation do not share this advantage. Also, including the step of antigenic stimulation would compromise the beneficial time factor of the assay of the invention, which is very quick to perform compared with prior art methods.

DETAILED DESCRIPTION OF THE PREFERRED EMBODIMENTS

Antigens to which antibodies for detection according to the method of the invention are directed include both bacterial and viral antigens. Clinically important antigens include, but are not restricted to those from for example Herpes Simplex virus, Cytomegalovirus, human immunodeficiency virus (HIV) and any of the Hepatitis viruses. Detection of such antigens could be used to rapidly establish whether patients are infected e.g. for blood screening purposes or for establishing and/or monitoring infection. The method is particularly useful owing to its simplicity and may be used when elaborate equipment is not available e.g. in field situations.

As used herein the terms "detecting" and "determining the amount of" encompass both quantitative and qualitative assessment of the level of antibody production, in the sense of obtaining an absolute value for the amount of antibody produced in the sample, and also an index, ratio, percentage or similar indication of the level of antibody production, as well as semi-quantitative or qualitative assessments.

A major advantage of the present invention is that only small sample volumes are required, eg. 50–500 μl, preferably 100–300 μl and commonly 100–200 μl, of blood, or blood product in a comparable volume to the whole blood source, in contrast to classical diagnostic tests which generally rely on several ml volumes of serum. This is especially useful in the case of blood sampling from neonates as the method of the invention requires only μl volumes.

The blood sample, generally a peripheral blood sample, may be used directly, although it may be preferable first to isolate lymphocytes from the sample. This can be done using standard techniques, well known in the art. Thus, for example, various whole blood preparations may conveniently be used eg. heparinized blood, EDTA-blood etc., such as are routinely prepared in clinical laboratories. Although not essential, erythrocytes present in the sample may be lysed eg. by using common methods of short-term exposure to distilled water or ammonium chloride, or by using other well-known haemolysis techniques. It will be appreciated that all enriched or purified preparations must contain the lymphocytes present in the whole blood from which the prepration is derived to allow detection of spontaneous antibody production. If desired, lymphocytes may be separated, for example using standard lymphocyte separation media eg. Lymphoprep (Nyegaard Co. Oslo, Norway), or using immunomagnetic separation (IMS) or a similar solid phase based separation system or other common techniques. In the case of IMS or similar separation techniques, a solid phase e.g. magnetic beads coated with antibody specific for certain sets of leucocytes may be used to separate the useful lymphocytes selectively. If separated lymphocytes are used, the cells may be washed prior to use, using standing washing methods. It has been observed however, that extensive washing of the cells is not required. Indeed, by not washing extensively, cell viability may be improved, and the method speeded up.

The blood sample, treated as mentioned above if required, or the separated lymphocytes are conveniently then contacted with a solid phase carrying an appropriate binding partner to immobilize the antibody or antibodies to be detected. Conveniently the binding partner is the test antigen or antigens, recognised by the antibody or antibodies to be detected. In one embodiment, the present invention thus provides a method of detecting active antibody production in a blood sample, said method comprising:

contacting, in the presence and absence of protein synthesis inhibitor, aliquots of said sample, or optionally, of lymphocytes directly isolated from said sample, with a solid phase carrying one or more antigens recognised by the antibody or antibodies to be detected;

detecting in solution, binding of antibody to said antigen (s); and comparing said antibody binding in the presence or absence of protein synthesis inhibitor, whereby to obtain a determination of the amount of active antibody secretion in response to said antigen(s).

Alternative binding partners may also be used, for example protein A, protein G or antibodies which recognise and bind to the antibody to be detected. In the latter case, highly specific binding is not required as specificity is introduced in this embodiment of the assay method by the subsequent binding of antigens which bind specifically to the antibodies to be detected. Thus in all embodiments a specific antigen-antibody complex is created. The presence of such complexes immobilized to the solid support is ascertained in the detection step of the method of the invention. The solid phase may be any of the well-known supports or matrices which are currently widely used or proposed for immobilisation, separation etc. These may take the form of particles, sheets, gels, filters, membranes, or microtitre strips, tubes or plates etc. and conveniently may be made of a polymeric material. However, for ease of operation and simplicity standard microtitre plates and wells may conveniently be used, preferably standard ELISA plates.

The solid phase may also be modified to permit detection of antibodies specific for a range of different antigens. Thus for example, discs or strips etc. of a suitable solid phase material eg. nitrocellulose or such like may be coated with different antigens and added simultaneously to a microtitre well or other suitable vessel, not containing any contacting antigen. Antibody binding detection methods may then be used to distinguish between the different antigens. Sets of discs each coated with relevant antigens consistent with a certain clinical condition or syndrome may be used in order to identify which of the suspected agents is causing the disease. The discs would then be individually processed in separate wells. This is a particularly material-saving procedure, since tests can be performed for simultaneous testing of a multiplicity of different antigens (either from the same infectious agent or from different agents relevant for the clinical syndrome or condition in each case) using the same small blood volume. An alternative approach is to use multiple blood samples in separate wells, each coated with different binding partners, e.g. antigens or antibodies, and develop the test accordingly.

Techniques for binding of the binding partner, e.g. antigen to the solid phase are also extremely well known and widely described in the literature. Many standard antigen coating procedures are described for example in ELISA and other solid phase Immunoassays, Theoretical and Practical Aspects; 1988, ed. D. M. Kemeny & S. J. Challacombe, John Wiley & Sons. If desired, the plates may be washed and blocked, again using standard techniques. Thus, for example, standard microtitre plates eg. ELISA plates may simply be coated with binding partner by incubating the plates overnight at 4° C. in a suitable buffer eg. phosphate buffered saline (PBS) containing the binding partner eg. at concentrations of 0.01 to 150 $\mu$g/ml protein, followed by blocking using appropriate blocking media (generally a cell culture medium) and incubating eg. at 37° C. for 1 to 5 hours. After removing the blocking solution the plates are ready for use.

Conveniently, however, the materials required to perform the method of the invention may be provided in kit form, where the solid support is supplied ready coated with binding partner and appropriately blocked.

As mentioned above, the contacting step generally involves incubating the sample or separated lymphocytes in the presence of the solid phase under conditions which permit antibody synthesis and secretion. Conveniently, standard ELISPOT incubation conditions may be used, as described for example in Czerkinsky et al., 1988 (supra). Generally, the sample or cells are incubated at 37° C. with 5% $CO_2$ in air when the medium in which the cells are incubated relies on $CO_2$ as part of the buffering system. $CO_2$-independent medium may also be used in which alternative buffering systems operate, such as media using the well-known HEPES constituent. In these cases, cells are simply incubated at 37° C. thus further simplifying the assay and its requirement for elaborate equipment. Incubation times may vary, but generally at least 1–2 hours are required. Incubation times of 2 to 6 hours, eg. 2 to 4 hours have been found to yield good results, although larger incubation periods eg. up to 12 or 24 hours, or overnight may in some situations be desirable. Appropriate media for incubation are well known in the art and include any standard cell culture media, eg. Dulbecco's modified Eagle's medium (DMEM) or RPMI or well-known cell culture media using HEPES as a $CO_2$-independent buffering system, containing appropriate sera eg. foetal calf serum (FCS) or other components eg. glutamine, as required. Optional additional components in the medium may include antibiotics eg. gentamycin, penicillin, streptamycin etc, other amino acids, growth factors etc.

It may be desirable to dilute the sample/cell suspension prior to the contacting step, and conveniently a range of cell/sample dilutions may be used. Dilution will generally be performed using the culture medium as diluent.

In order to distinguish ongoing antibody synthesis, incubation is performed in the presence and absence of protein synthesis inhibitor. Thus, prior to incubation, the inhibitor is added to part of the sample/cell aliquots, to block protein, and hence antibody, synthesis and parts are incubated without inhibitor. Any of the commonly known protein synthesis inhibitors may be used eg. cycloheximide. Concentrations of 10–5000 $\mu$g/ml may be used eg. 50–500 $\mu$g/ml cycloheximide.

It is preferable also to include an ATPase inhibitor such as sodium azide or other similar inhibitor with the protein synthesis inhibitor, in order quickly and fully to halt the cell's metabolism.

Following incubation, the sample/cells are removed from the solid phase. This may generally be accomplished simply by washing using a suitable medium eg. a buffer such as PBS. It has been found however that extensive washing is not required.

The solid phase is then subjected to the step of detecting binding of the antibody. The detection step, in terms of reading the signal, takes place in solution. Any of the known means of detecting antibody binding may be used, as long as a signal readable in solution is generated; for example depending on fluorescence, chemiluminescence, colorimetry or an enzyme reaction to produce the detectable signal. Conveniently, however an immunoassay may be used as the means of detection, and preferably an enzyme-linked immunosorbent assay (ELISA).

Immunoassay, and particularly ELISA, techniques are well known in the art and described in the literature (see for example ELISA and other solid phase Immunoassays, Theoretical and Practical Aspects; 1988, ed. D. M. Kemeny & S. J. Challacombe, John Wiley & Sons).

Following the removal of the sample/ cells, an enzyme-antibody conjugate may be added, for example in the ELISA detection method, which binds to the antibody bound to the antigen on the solid phase. Similarly, if the antibody to be detected is bound to the solid phase non-specifically via a binding partner, for example by an antibody against antibodies of a different species, an enzyme-antigen conjugate may be added which will bind specifically to the immobilized antibody to be detected. An enzyme substrate is then added in order to develop the detectable signal. In the present invention, a soluble substrate is conveniently used, yielding a signal detectable in solution. This is advantageous since it facilitates and simplifies the handling and processing of a large number of samples, and permits estimation of antibody production, although as mentioned above, absolute quantitation is not necessary, and if desired a qualitative or semi-quantitative result may be obtained. For convenience the substrate may be selected to yield a spectrophotometrically detectable signal, which may simply be read by reading absorbance, eg. using a standard ELISA plate reader. Indeed, standard ELISA reagents may be used, which has the advantage of rendering the assay of the invention compatible with existing methods and techniques routinely employed in clinical laboratories. However, other detection/signal generating systems may be used, yielding signals detectable by fluorescence, chemiluminescence etc.

Immuno-enzymatic amplification methods may also be used to improve the signal and increase sensitivity, for example using avidin-biotin methods such as the Extravidin system available from Sigma. Biotinylated secondary antibodies are used as ELISA reagents, in combination with a peroxidase avidin complex. Since one molecule of avidin is capable of binding several molecules of biotin, the use of avidin-biotin peroxidase complexes increases the surface concentration of peroxidase molecules, giving the method even greater sensitivity.

The materials and means required for the cell incubation (contacting) step and the antibody-binding detection step may also be conveniently supplied in kit form together with the binding partner-coated solid phase. The information obtained from the assay of the invention may be supplemented by using other assay methods. Additional and useful data on pre-existing serum/plasma antibodies may be obtained in a classical ELISA test. Additionally, after separation of lymphocytes from the blood sample, when this is performed, the remaining plasma fluid may be used for detecting pre-existing antibodies using the same binding partner-coated solid phase used in the assay of the invention.

In order to ensure that the assay method of the invention is working confidently, appropriate controls may be included. Firstly, the comparison between protein synthesis-blocked wells and unblocked wells will ensure that the invention is recording an acute antibody production by the test cells and not merely recording pre-existing antibodies from peripheral blood. In the case of using purified lymphocyte preparations as the sample, this will ensure that trace amounts of trapped antibodies from peripheral blood in the lymphocyte sample do not compromise the test. Secondly, to ascertain that the recorded difference between signals from blocked and unblocked wells is not due to sporadically and nonspecifically (bystander) activated lymphocytes, a negative control antigen is used. This antigen would be from an infectious agent most unlikely to be responsible for the acute disease of the patient, e.g. tetanus toxoid. The numbers of such bystander activated lymphocytes will in any event in all circumstances be much lower than required for a positive test result using the method of the invention. The design of the invention takes this point into account.

As mentioned above, due to its ease and speed of operation and simplicity, the assay of the invention, lends itself to diagnostic or other clinical or veterinary uses, e.g. fish-farming. In addition to small sample volumes, a further advantage is that only one sample is required, rather than serum pairs taken at a 2 to 3 week interval, such as is required in most conventional serological tests. Elaborate instrumentation is not required, and the assay is readily automated. In addition, it is readily possible to test for different immunoglobulin isotypes if required.

The afore-mentioned assay method of the invention provides one method for assessing the presence or extent of ongoing infection by virtue of the analysis of the spontaneous expression of specific antibodies to a defined antigen. Such a method is clearly applicable to the assessment of disease conditions which are known and to which antigens related to the relevant immunogen are available and thus provides a specific marker of infection. In some clinical situations however the specific disease or infection may not be identified and/or the appropriate antigen may not be available for use in the assay. In such cases, the assay may be modified to assess for the presence or extent of non-specific indicators of infection. Thus for example, lymphocyte-containing samples e.g. whole blood or purified or enriched lymphocyte preparations therefrom, may be examined with regard to their production of infection markers e.g. cytokines or interferons, for example interferon-γ.

Thus viewed from a yet further aspect the invention provides a method of detecting the presence of non-specific infection indicators in a blood sample, said method comprising:

contacting, in the presence and absence of protein synthesis inhibitor, aliquots of said sample, or optionally, of lymphocytes directly isolated from said sample, with a solid phase under conditions which permit production and secretion of infection indicators by the lymphocytes;

detecting in solution, binding of infection indicators to a binding partner on the solid phase; and comparing said infection indicator binding in the presence or absence of protein synthesis inhibitor, whereby to obtain a determination of the amount of infection indicators in said sample.

For performing this method, the solid phase may be provided with appropriate capture molecules, for example antibodies to the infection indicators for detection. For detection of the presence of said infection indicators immobilized on the solid phase, methods as described hereinbefore may be used, for example by the use of labelled antibodies or ligands. In this method, specific markers may be identified by appropriate choice of the immobilizing moiety or detection molecule. Thus, for example, all protein in the sample may be immobilized on the solid support and detection may be performed using a labelled specific antibody or ligand. Alternatively, a specific binding partner may be used to immobilize pertinent infection indicators which may then be labelled appropriately, either positively or negatively, for example in the former case by binding to a domain present on the infection indicator but not exclusive to that molecule, or in the second case by labelling unbound binding partner on the solid phase. Kits for performing this method also form part of this invention.

EXAMPLES

The invention will now be described in more detail with reference to the following non-limiting Examples, in which the assay method of the invention is referred to as the Plasmacute assay.

Example 1

General Procedure

Cells: Heparinized blood taken at various times post-vaccination from volunteers being given inactivated influenza vaccine. Blood mixed with an equal volume PBS. Lymphocytes separated by Lymphoprep (Nyegaard & Co, Oslo). Cells washed twice in PBS, resuspended (dilutions) in Dulbecco's Modification of Eagle's Medium supplemented with 20% FCS, 2 mM L-glutamine, 100 IU/ml pencillin and 100 μg/ml streptomycin (Pen+Strep)=MEDIUM.

STOP solution: 1 mg/ml cycloheximide made up in PBS containing 10% sodium azide.

ELISA and influenza antigens: Purified surface antigens from the three virus strains in the influenza vaccine being used in a clinical trial, here designated for short H3N2, H1N1 and B.

ELISA plates: Greiner EIA plates 655001 F-form, or Costar EIA plates 3590. Coating with 100 µl/well with a solution of 10 µg/ml protein in PBS overnight at 4° C. Blocking with MEDIUM for 1 hour at room temperature. Wash once with PBS.

TEST: 100 µl dilutions of cell suspensions in MEDIUM added to triplicate wells in two parallel sets for each of the three influenza antigens. One set of triplicate wells are blocked at the initial step adding 50 µl of STOP solution. Incubated at various times at 37° C. in an incubator with 5% $CO_2$ in air. The ELISA plate is washed once with PBS, then twice with PBS with 0.05% Tween 20. Fifty µl/well of appropriately diluted rabbit anti-human Ig peroxidase conjugate (Sigma) is added and left at room temperature for 1 hour. The plate is subsequently developed using o-phenylene diamine (OPD) substrate and absorbance is read at 492 nm.

Blood sampled 11 days post-vaccination

Cell incubation time: 4 hours, 0 hours=blocked wells

| | No of cells | H3N2 | H1N1 | B |
|---|---|---|---|---|
| 0/4 hrs | $6.6 \cdot 10^4$ | 264/522 | 199/490 | 352/527 |
| 0/4 hrs | $6.6 \cdot 10^3$ | 238/290 | 143/194 | 331/353 |

All entries are mean of triplicate wells as absorbance×1000. range±10%.

Conclusion: $6.6 \cdot 10^4 = 66,000$ cells give a significant signal increase at 4 hours incubation. H3N2 absorbance goes up 98%, H1N1 up 153% and B up 50%.

This is a representative experiment. Additional tests showed that overnight incubation of cells gives an even more clear distinction between blocked and unblocked wells with absorbances over 1000. The system also works for shorter incubation times, eg. 2–3 hours 0.10-fold more cells, eg. $6.6 \cdot 10^3$ cells/well may also, but not always, give a clearer distinction.

Example 2

General Procedure

Cells: Heparinized blood taken at 7 days post-vaccination from volunteers being given inactivated influenza vaccine. Blood mixed with an equal volume PBS. Lymphocytes separated by Lymphoprep (Nyegaard & Co, Oslo). Cells washed twice in PBS, resuspended in Dulbecco's Modification of Eagle's Medium supplemented with 20% FCS, 2 mM L-glutamine, Pen+Strep (as previous)=MEDIUM.

STOP solution: 1 mg/ml cycloheximide made up in PBS containing 10% sodium azide.

Test antigens: Purified surface antigens from the three virus strains in the influenza vaccine being used in the clinical trial, here designated for short H3N2, H1N1 and B.

Control antigen: Tetanus toxoid (Non-aluminium adsorbed; Lederle).

ELISA plates: Greiner EIA plates 655001 F-form, or Costar EIA plates 3590. Coating with 100 µl/well with a solution of 10 µg/ml protein in PBS overnight at 4° C., tetanus: 10 Lf/ml. Blocking with MEDIUM for 1 hour at room temperature. Wash once with PBS.

TEST: 100 µl dilutions of cell suspensions in MEDIUM added to triplicate wells in two parallel sets for each of the three influenza antigens and tetanus control antigen. One set of wells are blocked at the initial step adding 50 µl of STOP solution. Incubated at 37° C. in an incubator with 5% $CO_2$ in air for 3 hours. After incubation, the ELISA plate is washed once with PBS, then twice with PBS with 0.05% Tween 20. Fifty µl/well of appropriately diluted rabbit anti-human Ig peroxidase conjugate (Sigma) is added and left at room temperature for 1 hour. The plate is subsequently developed using o-phenylene diamine (OPD; Sigma) substrate and absorbance is read at 492 nm. [The test can be modified to increase sensitivity, by an additional step before substrate by using an 1 hour Extravidin/peroxidase step (Sigma). This requires use of biotinylated conjugate in lieu of peroxidase conjugate (Sigma)].

Representative experiments result (No extravidin):

7 days post-vaccination (2 subjects; #1 and #2)

Cell incubation time: 3 hours, 0 hours=blocked wells

| | No of cells | H3N2 | H1N1 | B | Tetanus |
|---|---|---|---|---|---|
| 0/3 hrs | $10^5$ #1 | 063/410 | 055/269 | 206/258 | 046/050 |
| | #2 | 045/077 | 048/242 | 182/207 | 040/046 |

All entries are mean of triplicate wells as absorbance×1000. Range±16%.

The subjects are teenagers (16 years). It is well known that youngsters respond particularly well to A/H1N1 influenza vaccine. This is clearly seen above, both subjects #1 and #2 respond well. However, usually vaccinees respond differently to the various vaccine components, so that difference in absorbance increase must be expected. This is demonstrated here when subject #1 responded poorly to the B virus, whereas #2 only responded significantly to the H1N1 virus. As expected, none of them responded to the tetanus toxoid. If however, cells had been stimulated in vitro with toxoid for a time period of several days, their immunological earlier memory (through childhood vaccination) might have resulted in a tetanus antibody production. In a real infectious case assayed in a diagnostic laboratory using the invention, only one test agent/antigen will be giving a positive signal.

Example 3

General Procedure

Cells: Heparinised blood taken 6 days post-vaccination from an adult (male aged 24 years) and a child (male aged 3 years) having received inactivated subunit influenza vaccine. Lymphocytes were separated as described under Examples 1 and 2. Cells were contacted with the solid phase carrying antigen H3N2, H1N1 and B as described in Examples 1 and 2 for 3 hours at 37° C., and the test developed as described (no STOP solution or Control antigen used in this experiment).

Table 1 shows the results from the two individuals in which the reading for each antigen are mean of triplicate wells as absorbance x1000.

TABLE 1

| Adult subject | | | | Child subject | | | |
|---|---|---|---|---|---|---|---|
| Number of cells (thousands) | A/H3N2 | A/H1N1 | B | Number of cells (thousands) | A/H3N2 | A/H1N1 | B |
| 224 | 475 | 322 | 913 | 275 | 1268 | 97 | 10 |
| 112 | 189 | 193 | 567 | 138 | 951 | 65 | 10 |
| 56 | 93 | 62 | 162 | 69 | 672 | 51 | 20 |

The results show that the small child, having only had one earlier influenza episode, an A/H3N2 infection, gave a very strong immune response to the A/H3N2 component in the trivalent vaccine. As expected for this child, there was no response to the A/H1N1 and B components. Such small children usually require 2 doses of vaccine at some weeks interval to give a satisfactory immune response. About 70,000 lymphocytes, corresponding to about 70 µl volume of full blood, were sufficient to give a definite positive result. For the adults subject, having had multiple influenzal episodes, the response was not as vigorous, but nevertheless significant to all three components of the vaccine, albeit to varying degree. For the B-component approximately 100,000 lymphocytes were necessary to give a positive response, whereas the two A components required minimally 100,000 cells, preferably 200,000 cells.

Experiment 4

Detection of Herpes Simplex Type 2 by Classical and Phasmacute Assay Methods

General Procedure

Tissue Culture and serological analyses

Material from the genitalia of five subjects having presented with symptoms suggestive of a genital herpes virus infection were subjected to routine tissue culture procedures attempting to detect replicating virus from the specimens (performed by the Virus Laboratory, Haukeland University Hospital, Bergen). The same laboratory performed routine serological analyses of serum samples using commercial ELISA kits (Behringer Enzygnost from Behringer, Germany) containing HSV antigens to detect IgG and IgM.

Separation of lymphocytes

Lymphocytes were isolated by lymphoprep (Nycomed) density gradient centrifugation of heparinised blood from the five subjects having presented with symptoms suggestive of a genital herpes virus infection, taken simultaneously with the hospital samples. The cells were washed thrice in PBS and resuspended in culture medium of DMEM containing 20% FCS, 1 mM L-glutamine, 50 IU/ml penicillin and 50 µg/ml streptomycin (DMEM/FCS). Viable cells were counted by trypan blue exclusion (0.2%).

Plasmacute assay using Behringer Enzygnost anti-HSV IgM and IgG ELISAs

Behringer Enzygnost anti-HSV IgM and IgG are supplied as strips containing 8 wells coated with antigen derived from permanent simian kidney cells infected with HSV and 8 wells coated with control antigen from non-infected cells. Strips were blocked with 200 µl/well of DMEM/FCS at 37° C. in 5%. $CO_2$ for 1 hour. One hundred µl per well of the appropriate dilution of lymphocytes was added and incubated for 3 hours at 37° C. in 5% $CO_2$. All the following procedures were strictly according to the instructions given by the supplier of the kit. Plates were developed using conjugates, reagents and buffers supplied by the same supplier. The substrate, tetramethylbenzidine hydrochloride (TMB), required reading ODs at 450 nm, using the available Titertek Multiskan MCC/340 plate reader (Flow Laboratories).

Plasmacute assay using Bioelisa HSV-2 IgG

Bioelisa IgG HSV-2 ELISA (BIOKIT, Spain) is supplied as strips containing 8 wells which are coated with inactivated HSV-2 antigen. Strips were blocked with 200 µl/well of DMEM/FCS at 37° C. in 5% $CO_2$ for 1 hour. One hundred µl per well of the appropriate dilution of lymphocytes was added and incubated for 3 hours at 37° C. in 5% $CO_2$. All the following procedures were strictly according to the instructions given by the supplier of the kit. Plates were developed using conjugates, reagents and buffers supplied by the same supplier. The substrate, tetramethylbenzidine hydrochloride (TMB), required reading ODs at 450 nm, using the available Titertek Multiskan MCC/340 plate reader (Flow Laboratories).

Plasmacute assay using Bioelisa HSV IgM (Immunocapture) assay

Bioelisa HSV IgM (Immunocapture) assay (BIOKIT, Spain) is supplied as strips containing 8 wells which are coated with rabbit anti-human IgM antibodies. Strips were blocked with 200 µl/well of DMEM/FCS at 37° C. in 5% $CO_2$ for 1 hour. One hundred µl per well of the appropriate dilution of lymphocytes was added and incubated for 3 hours at 37° C. in 5% $CO_2$. All procedures were performed according to the manufacturer's instructions. Specifically, bound antibody was detected with 100 µl/well of HSV antigen labelled horseradish peroxidase (purified and inactivated HSV which has been propagated in vitro in human fibroblasts) and to minimise non-specific reactions unlabelled control antigen, consisting of uninfected cellular components (supplied with the kit), 10 µl HSV antigen and 10 µl control antigen per strip. Plates were read in a Titertek Multiskan MCC/340 plate reader at 450 nm (Flow Laboratories).

The results of the experiment are shown in Table 2.

TABLE 2

| Patient | Time after onset of symptoms (days) | SEX/AGE | Suspected primary/recurrent infection | Virus isolation | Serum antibodies (Behringer ELISA) IgM | Serum antibodies (Behringer ELISA) IgG | Plasmacute assays Behringer IgM | Plasmacute assays Behringer IgG | Plasmacute assays Bioelisa IgG | Capture antibody Plasmacute assay Bioelisa IgM |
|---|---|---|---|---|---|---|---|---|---|---|
| 1 | 6 | F/40 | Primary infection | –ve | – | Borderline | — | 205 000 | 103 000 | — |
| 2 | 6 | F/21 | Primary infection | HSV-1 | – | + | — | 223 000 | 111 000 | — |
| 3 | 2 | M/47 | Recurrent infection | HSV-2 | – | + | — | 48 000 | 96 000 | — |
|   | 20 |   |   | HSV-2 | + | nt | 182 000 | nt | — | — |
| 4 | 5 | F/22 | Primary infection | –ve | Borderline | + | 60 500 | 15 000 | 121 000 | <8 000 |
|   | 19 |   |   |   | nt | nt | — | 40 500 | 20 250 | 40 500 |
| 5 | 7 | F/21 | Primary infection | –ve | – | – | — | — | — | — | nt = not tested.

Table 2 summarizes the data for patients 1–5. The diagnostic laboratory at Haukeland University Hospital attempted isolating the virus from clinical specimens and also carried out routine ELISA tests for serum IgG and IgM using the Behringer Enzygnost ELISA kits. The type of virus isolated is stated, –ve means negative isolation. Serum ELISA cut-off values are defined by the manufacture of the kit; +=OD>0.2, borderline=OD 0.1–0.2, defined as an equivocal result by the manufactures of the assay; and -–=OD<0.1.

For the Plasmacute assay we have used the OD>0.2 as positive and have tabulated the numbers of lymphocytes necessary to give such a response.

Only the Bioelisa IgG test claims to identify HSV2 antibodies, whereas the others will indicate infection with HSV (1 and/or 2).

Results

Patient 1 had clinical symptoms of a primary HSV-2 infection. The hospital tests failed to isolate virus from the clinical sample and no IgM was found by standard ELISA assays. Borderline serum IgG antibody was found by the standard hospital ELISA tests. In confirmation with these results, there were no cells found to be producing IgM antibody in the Plasmacute assay. Both the Behringer IgG and Bioelisa IgG Plasmacute assays detected cells producing IgG antibody to HSV. 205000 lymphocytes were required to give the cut-off absorbance in the Behringer Plasmacute assay and in the Bioelisa IgG 103 000 lymphocytes were required to give the cut-off absorbance.

Patient 2 was undergoing a primary infection which was confirmed by virus isolation as HSV type-1. No serum IgM was detected by the hospital laboratory, but IgG antibody was detected. In the Plasmacute assay no cells producing IgM were detected, however both the Behringer and Bioelisa Plasmacute assay detected IgG producing cells, 223 000 and 111 000 cells were required respectively.

Patient 3 had a recurrent HSV-2 infection, which was confirmed by isolation of HSV-2 virus from clinical specimens. IgG was present in a serum sample taken 2 days after onset of clinical symptoms, however no serum IgM was detected at this time. In the Plasmacute assay no IgM was detected at 2 days after onset of clinical symptoms, however both the Behringer and Bioelisa Plasmacute assays detected IgG producing cells (48 000–96 000 cells required). IgM serum antibodies were detected by the hospital in a serum sample taken 20 days after onset of the clinical symptoms. 182 000 cells were required to produce a cut-off absorbance in the Plasmacute Behringer IgM assay, however no cells were detected by the Bioelisa IgM Plasmacute assay.

Patient 4 had a primary infection with HSV. No virus was detected in the clinical sample sent to the hospital laboratory. Borderline serum IgM antibodies were detected and positive levels of serum IgG antibodies were found. Both IgM and IgG antibodies were detected in the Plasmacute assay using both the Behringer and Bioelisa kits in blood samples taken 5 and 19 (no Behringer IgM detected) days after onset of clinical symptoms. In the Plasmacute assay, less than 8000 cells were required for the Bioelisa IgM assay and 60 500 cells were required for the Behringer IgM assay, both of which would require less than 100 μl heparinised blood.

Patient 5 was suspected of having a primary infection with HSV. However no virus was isolated by the laboratory and the no serum antibodies were detected. In the Plasmacute assay no cells were detected producing either IgG or IgM antibody to HSV.

Discussion

The Plasmacute assay has been demonstrated to work both for primary and recurrent herpes virus infections. In all instances the Plasmacute assay performed at least equally well as the traditional ELISA procedures used herein. In particular, for Patient 1, although no virus was isolated from the clinical sample, and scoring only borderline positive (i.e. non-conclusive) by the Hospital routine assay, the Plasmacute assay (Bioelisa IgG and Behringer IgG) showed that approx. 100,000 cells and 200,000 cells, respectively, gave an unequivocal positive result. It is possible that this patient has a double infection (HSV1 and HSV2), of which only HSV1 was recovered from the site by virus isolation. It cannot be ruled out, however, that the positive HSV2 result (Bioelisa IgG) was caused by serological cross-reaction. For the two time-spaced samples from Patient 4, from whom no virus was isolated, the Plasmacute assay showed the shift of numbers of herpes specific IgM- and IgG-producing lymphocytes from the earlier phase to the later phase of the infection, consistent with the well-known dynamics following a primary infection, clearly confirming an active immune response. The Bioelisa IgM Plasmacute test was particularly sensitive, as less than 8,000 lymphocytes were required to give a positive signal in the first of the two samples.

We have in this experiment showed that the Plasmacute method works for clinical cases of viral infections in man.

Experiment 5
Multiple Discs—Coating of Nitrocellulose Discs with Capture Antibodies Specific for IgG, IgA and IgM Antibodies This experiment was performed to establish if a multiple disc system could be used in the Plasmacute assay to detected antibodies of different specificities.

General Procedure

Heparinized full blood samples were drawn from two healthy adults subjects. Since these subjects were not in an acute phase of any infection, we aimed at analyzing the IgG, IgM and IgA spontaneous antibody secretion irrespective of their (unknown) antigenic specificity.

μl/well of o-phenylediamine dihydrochloride (OPD) (Sigma P-7288) in 0.05M phosphate citrate buffer (pH 5.0). Thirty minutes after addition of the substrate the development was stopped using 100 μl/well of 1 M $H_2SO_4$. One hundred μl per well was transferred to a 96 well ELISA plate (Greiner EIA plates 655001 F-form) and the ODs were read in a Titertek Multiskan MCC/340 plate reader (Flow Laboratories) at 492 nm.

The results of the experiment are shown in Table 3 in which the reading for each captive antibody are mean of triplicate wells as absorbance x1000.

TABLE 3

| | Subject 1 | | | | Subject 2 | | | | | |
|---|---|---|---|---|---|---|---|---|---|---|
| | Well 1 | | | Well 2 | | | Well 3 | | | Well 4 | |
| Disc Number | Anti-human capture antibody | OD (492 nm) | Disc Number | Anti-human capture antibody | OD (492 nm) | Disc Number | Anti-human capture antibody | OD (492 nm) | Disc Number | Anti-human capture antibody | OD (492 nm) |
| 1 | IgG | 405 | 1 | IgG | 148 | 1 | IgA | 182 | 1 | IgM | 82 |
| 2 | IgA | 140 | 2 | IgG | 182 | 2 | IgA | 202 | 2 | IgM | 107 |
| 3 | IgM | 85 | 3 | IgG | 112 | 3 | IgA | 221 | 3 | IgM | 124 |
| 4 | IgG | 410 | 4 | IgG | 157 | 4 | IgA | 263 | 4 | IgM | 145 |
| 5 | IgA | 125 | 5 | IgG | 142 | 5 | IgA | 190 | 5 | IgM | 119 |
| 6 | IgM | 64 | 6 | IgG | 123 | 6 | IgA | 209 | 6 | IgM | 127 |
| 7 | IgG | 375 | 7 | IgG | 144 | 7 | IgA | 172 | 7 | IgM | 138 |
| 8 | IgA | 168 | 8 | IgG | 125 | 8 | IgA | 151 | 8 | IgM | 134 |
| 9 | IgM | 61 | | | | | | | | | |
| Cells | | | Cells | | | Cells | | | Cells | | |

Subject 1 was used to establish if a system using discs coated with 3 different antigens could be used in a single well in the Plasmacute assay. One well (No. 1).

Subject 2 was used to establish if there was a weakening of the signal in the presence of a number of discs coated with the same antigen. Three separate wells in the Plasmacute assay (wells No. 2, 3 and 4).

Separation of lymphocytes

Lymphocytes were isolated by lymphoprep (Nycomed) density gradient centrifugation of heparinised blood. The cells were washed thrice in PBS and resuspended in culture medium of DMEM containing 20% FCS, 1 mM L-glutamine, 50 IU/ml penicillin and 50 μg/ml streptomycin (DMEM/FCS). Viable cells were counted by trypan blue exclusion (0.2%). Plasmacute assay using discs as the solid phase Mixed esters of cellulose discs with 8 μM pore size (Millipore SCWP 013 00) were coated with 10 μg/ml of goat anti-human class specific antibodies (Sigma, anti-IgG I-3382; anti-IgA I-0884; anti-IgM I-0759) diluted in PBS azide (0.00%) overnight at room temperature. Discs were blocked with DMEM/FCS at 37° C. in 5% $CO_2$ for 1 hour. Lymphocytes were added to a 12 mm clear transwell with pore size 0.4 μM (Costar 3460) and the discs placed underneath, and incubated for 3 hours at 37° C. in 5% $CO_2$. Individual discs were transferred to the separate wells of a 24 well plate (Costar) and washed 3× with PBS and 3× with PBS Tween (0.05%). Bound antibody was detected with 200 μl/well of goat anti-human class-specific peroxidase conjugated antibodies (Sigma IgG A-6029, IgA A-4165, IgM A-4290) diluted in DMEM/FCS and incubated for 2 hours at room temperature. Discs were washed to remove unbound antibody as described previously and developed using 200

Well 1 contained 2 million lymphocytes, wells 2–4 contained 1 million lymphocytes. The "cell" reference is to indicate which disc number was located closest to the cell layer.

Results

The test with subject 1 showed that even 9 discs could easily be used in the well containing the lymphocytes. The response for the three IgG discs, the three IgA discs and the three IgA discs were for all practical purposes identical for each set, thus showing that the actual position of a disc relative the antibody-secreting lymphocytes was not critical. The test with lymhocytes from subject 2 showed that at least 8 identically coated wells could be placed in one lymphocyte-containing well to give virtually identical readings. Thus, the invention allows for multiple assays for the same lymphocyte preparation in one well.

What is claimed is:

1. A method of detecting active antibody production in response to target antigen in a blood sample, said method comprising:
   a) contacting at least one first aliquot of said sample in the absence of a protein synthesis inhibitor and at least one second aliquot in the presence of protein synthesis inhibitor, each aliquot with a solid phase under conditions which permit antibody production and secretion by a lymphocyte;
   b) generating a signal readable in solution and detecting the signal in solution to detect antibody binding to said antigen(s) on one or more solid phases in each aliquot; and c) comparing said signal of antibody binding from the first and second aliquots to determine the amount of active antibody secretion in response to said antigen(s), wherein the difference between the signals of the first and second aliquots indicate the antibody production with response to the target antigen(s).

2. A method as claimed in claim 1 wherein said one or more solid phases carries one or more antigens recognized by the antibody or antibodies to be detected.

3. A method as claimed in claim 1 wherein said solid phase carries one or more antibodies which recognize the antibody or antibodies to be detected.

4. A method as claimed in claim 1 wherein said blood sample has a volume of less than 1 ml.

5. A method as claimed in claim 1 wherein the method is performed on neonate or infant blood samples for distinguishing between newly synthesised antibodies and passively transferred maternal antibodies.

6. A method as claimed in claim 1 wherein said blood sample is obtained by purification or enrichment procedures of blood taken directly from a patient.

7. A method as claimed in claim 1 wherein said lymphocyte is directly isolated from said sample.

8. A method as claimed in claim 1 wherein the solid phase is incubated with blocking media prior to the contacting step.

9. A method as claimed in claim 1 wherein the protein synthesis inhibitor is cycloheximide used at a concentration of about 50–500 $\mu$g/ml.

10. A method as claimed in claim 1 wherein an ATPase inhibitor is used in conjunction with the protein synthesis inhibitor.

11. A method as claimed in claim 1 wherein the detecting step is performed by immunoassay.

12. A method as claimed in claim 11 wherein the immunoassay is ELISA.

13. A method as claimed in claim 3 wherein one or more antigens recognized by the antibody or antibodies to be detected are contacted with said solid phase on which said antibody or antibodies to be detected are bound.

14. A method as claimed in claim 2 wherein one or more antibodies which recognized the antibody or antibodies to be detected are contacted with said solid phase on which said antibody or antibodies to be detected are bound.

15. A method as claimed in claim 1 wherein a soluble substrate is used for the detection step and yields a spectrophotometrically detectable signal.

16. A method as claimed in claim 1 wherein a negative control antigen is used.

17. A method as claimed in claim 1 wherein active antibody production to Herpes virus is detected.

18. A method as claimed in claim 2 wherein one or more solid phases are employed each bearing a different target antigen.

19. A method of detecting the presence of non-specific infection indicators in a blood sample, said method comprising:
contacting, in the presence and absence of protein synthesis inhibitor, aliquots of said sample, or optionally, of lymphocytes directly isolated from said sample, with a solid phase under conditions which permit production and secretion of infection indicators by a lymphocyte;
generating a signal readable in solution and detecting the signal in solution to detect binding of infection indicators to a binding partner on the solid phase; and
comparing said signals of infection indicator binding in the presence or absence of protein synthesis inhibitor to determine the amount of infection indicators in said sample, wherein the difference between the signals indicate the production an secretion of infection indicators by the lymphocyte.

20. A method as claimed in claim 1, wherein the aliquots are selected to be lymphocytes directly isolated from the sample.

21. A method as claimed in claim 1 wherein said detection is quantitative.

22. A method as claimed in claim 4 wherein the aliquots are isolated lymphocytes.

* * * * *